United States Patent [19]

Arima et al.

[11] Patent Number: 5,073,545
[45] Date of Patent: Dec. 17, 1991

[54] AGENT CONTAINING AN ELLAGIC ACID SERIES COMPOUND FOR EXTERNAL APPLICATION AND USE THEREOF

[75] Inventors: Masatoshi Arima, Odawara; Hiroaki Nishizawa, Fujisawa; Keiji Takeuchi, Tokyo; Hiroshi Deura, Yotsukaidou; Keiichiro Ishida, Tokyo, all of Japan

[73] Assignee: Lion Corporation, Tokyo, Japan

[21] Appl. No.: 202,321

[22] Filed: Jun. 6, 1988

[30] Foreign Application Priority Data

Jun. 9, 1987 [JP] Japan .................................. 62-143507
Mar. 24, 1988 [JP] Japan .................................. 63-70396

[51] Int. Cl.$^5$ ...................... A61K 31/70; A01N 43/16
[52] U.S. Cl. ......................................... 514/27; 514/53; 514/453; 424/195.1
[58] Field of Search ................ 549/278; 536/4.1, 18.1; 514/25, 27, 53, 453; 424/195.1

[56] References Cited

U.S. PATENT DOCUMENTS 3,576,007  4/1971  Hochstein ........................... 549/278
3,694,557  9/1972  Persinos .............................. 424/279
4,696,813  9/1987  Higa ....................................... 424/59

FOREIGN PATENT DOCUMENTS 0145880  9/1982  Japan ................................... 549/278
58-038209  3/1983  Japan .

OTHER PUBLICATIONS

Murhtar et al., Chemical Abstracts, vol. 100(21), No. 169716g, "Protection against 3-methycholanthrene-induced skin . . . ".

Takahashi et al., "The components of the plants of Lagerstroemia genus", Chemical Abstracts, vol. 87(21), 1977, No. 164237e.

Chemical Abstracts, vol. 103, No. 7, Aug. 19, 1985, p. 464, No. 52695v, Columbus, Ohio, U.S.; M. K. Quinn et al.: "Isolation and identification of ellagitannins from white oak wood and an estimation of their roles in wine".

Primary Examiner—Johnnie R. Brown
Assistant Examiner—Elli Peselev
Attorney, Agent, or Firm—Burns, Doane, Swecker & Mathis

[57] ABSTRACT

Agents for external application contain as an effective component ellagic acid series compounds represented by the general formula [I] or salts thereof:

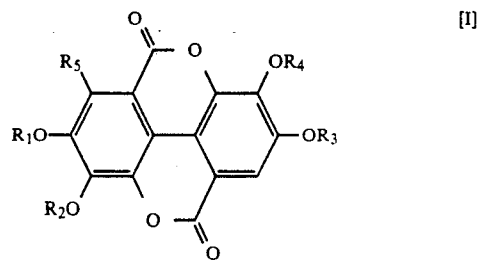

wherein $R_1$ to $R_4$ are a hydrogen atom, an alkyl group having 1 to 20 carbon atoms, an alkoxy group having 1 to 20 carbon atoms, a polyalkylene oxide residue where the alkylene oxide unit has 2 to 3 carbon atoms, or a sugar residue represented by the formula [II]:

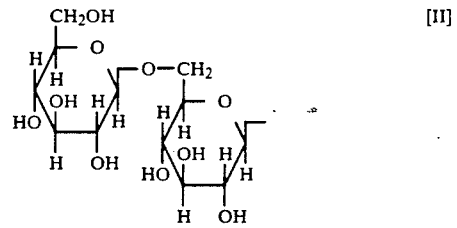

and $R_5$ is a hydrogen atom, a hydroxyl group or an alkoxy group having 1 to 8 carbon atoms.

10 Claims, No Drawings

AGENT CONTAINING AN ELLAGIC ACID SERIES COMPOUND FOR EXTERNAL APPLICATION AND USE THEREOF

BACKGROUND OF THE INVENTION

1. Field of the Invention

This invention relates to an agent for external application, particularly agent to be applied to the skin having excellent skin lightening and whitening effect for face care and body care and use thereof.

2. Description of the Prior Art

Cosmetics having a skin lightening and whitening effect are of very great interest to consumers, and there have hitherto been used as effective components peroxides such as hydrogen peroxide, zinc peroxide and magnesium peroxide, ascorbic acid, glutathione, colloidal sulfur, and various natural substances. However, hydrogen peroxide and ascorbic acid have problems regarding stability, preservability, etc., and moreover it is hard to say that their effects are adequate. Further, glutathione and colloidal sulfur have a peculiar smell, which causes a problem when it is added to cosmetic composition.

Further, hydroquinone is used as a skin-decoloring agent in U.S.A., etc., but it has a problem in view of safety (irritating property and allergic property) when compounded into cosmetics.

Therefore, there have been developed various cosmetics which do not have the above problems and can produce a skin lightening and whitening effect on the skin. There have been developed, for example, agents for external application using kojic acid and kojic acid derivatives [Japanese Patent Publication for Opposition Purpose (hereinafter referred to as "J. P. KOKOKU") No. 56-18569, Japanese Patent Unexamined Published Application (hereinafter referred to as "J. P. KOKAI") No. 53-3538, and J. P. KOKOKU Nos. 61-60801, 58-22151 and 60-9722], cosmetics containing quercetin as an effective component (J. P. KOKAI No. 55-92305), cosmetics containing fatty acid esters of quercetin as effective components (J. P. KOKAI No. 58-131911), cosmetics containing catechin, etc. as effective components (J. P. KOKAI No. 52-44375), etc. However, in practical use, these entail various problems such that the stability of the fresh components is inadequate, because their effects are not adequately exhibited in animals and human beings even though their effects at the cell level are noticeable.

SUMMARY OF THE INVENTION

It is, therefore, a primary object of the invention to provide an agent for external application such as cosmetics which are excellent in stability and safety and give a skin lightening and whitening effect.

Other objects of the invention are to provide use thereof for giving a skin lightening and whitening effect.

The invention has been completed based on the finding that ellagic acid series compounds have an excellent skin lightening and whitening effect, and moreover, when used in agent for external application such as cosmetics have no irritating or sensitizing properties and have good stability over the lapse of time.

In accordance with the invention, there is provided an agent for external application comprising at least one of ellagic acid series compounds represented by the general formula [I]:

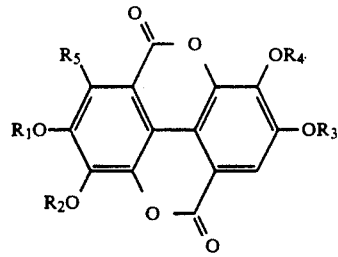

wherein $R_1$ to $R_4$ are a hydrogen atom, an alkyl group having 1 to 20 carbon atoms, an alkoxy group having 1 to 20 carbon atoms, a polyalkylene oxide residue where the alkylene oxide unit has 2 to 3 carbon atoms, or a sugar residue represented by the formula [II]:

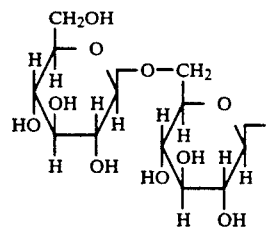

and $R_5$ is a hydrogen atom, a hydroxyl group or an alkoxy group having 1 to 8 carbon atoms.

The present invention further provides use thereof for giving a skin lightening and whitening effect.

DETAILED DESCRIPTION OF THE INVENTION

Preferred ellagic acid series compounds among those of the general formula [I] used in the invention are ellagic acid where $R_1$ to $R_5$ are all hydrogen atoms and those where $R_1$ to $R_4$ are hydrogen atoms, methyl groups or ethyl groups and $R_5$ is a hydrogen atom, a hydroxyl group or a methoxy group. Salts of the above compounds can also be used in the invention, and include salts with alkali metals such as sodium and potassium, salts with alkali earth metals, ammonium salts, amine salts, etc., but salts where a part of phenolic hydroxyl groups has become an alkali metal salt are preferable in view of solubility and the like.

In order to adjust the lipophilic property or hydrophilic property of ellagic acid series compounds in preparation of cosmetics, there can be used compounds in which some of $R_1$ to $R_4$ in the formula [I] are long-chained alkyl or alkoxy groups or residues of alkylene oxide condensates such as polyoxyethylene wherein the alkylene groups have 2 to 3 carbon atoms. This applies similarly to $R_5$.

Specific examples of the above ellagic acid series compounds include ellagic acid, 3,4-di-O-methylellagic acid, 3,3',4-tri-O-methylellagic acid, 3,3'-di-O-methylellagic acid, 3,3',4,4'-tetra-O-methyl-5-methoxyellagic acid, 3-ethyl-4-methyl-5-hydroxyellagic acid, Amritoside and various salts of these compounds, and mixtures of two or more thereof.

When an ellagic acid series compound of the above general formula [I] is an acidic substance in the invention, a part of the acid is neutralized with an alkali metal in form of hydroxide, carbonate or the like, and use of thus obtained salt brings about enhancement of water dispersibility, eliminates the problem of bad dispersibility in preparation of agents for external application, and brings about the advantages that the products are excellent in appearance and preservability and better in skin lightening and whitening effect. Such a partially neutralized salt is desirably obtained by dissolving ellagic acid in an aqueous solution of pH 12 to 14, preferably of an alkali metal hydroxide, adjusting the pH to 5 to 8 with an acid (either an inorganic acid or an organic acid can be used, but sulfuric acid is preferable in view of after-treatment) and collecting the partially neutralized salt as the precipitate. Even when ellagic acid of low purity is used, impurities such as tannin are effectively removed from obtained partially neutralized salts by this method, and therefore thus obtained salts have good appearance and a color tone free of black tincture. If insoluble matters are observed when ellagic acid is dissolved in the above aqueous alkali metal solution, it is desirable to remove them by a conventional method such as filtration or centrifugation. Further, when ellagic acid of a low purity is used, it is desirable to remove the impurities in advance by adsorption treatment on active carbon, etc.

These ellagic acid series compounds can readily be obtained according to, for example, the method described in J. P. KOKOKU No. 53-14605 from natural substances such as *Eucalyptus cortex, Arctostaphylos uva-ursi folium, Granati cortex, Phyllanthus emblica fructus, Sapium sebiferum folium, Rhus chinensis folium, Acacia catechu, Platycarya strobilacea cortex, Terminalia chebula cortex, Camptotheca acuminata radix, Polygonum bistorta rhizoma, Lagerstroemia subcostata folium, Sapium discolor rhizoma, Sapium discolor folium, Bischofia javanica radix, Lythrum salicaria herba, Geranium pratense rhizoma, Euphorbia hirta herba, Phyllanthus urinaria herba, Eucalyptus citriodora folium, Euphorbia royleana, Psidium guajava fructus, Psidium guajava cortex, Mangifera indica fructus, Cynips gallae tinctoriae, Syzygium cumini semen, Syzygium cumini cortex, Phyllanthus emblica radix, Phyllanthus emblica cortex, Phyllanthus emblica folium, Agrimonia pilosa radix, Psidium guajava folium, Sapium sebiferum cortex, Lagerstroemia indica radix, Phyllanthus urinaria herba and Geranium herba.*

Ellagic acid series compounds used in the invention widely exist in natural substances, and are thought to have very high safety. However, by way of precaution, safety of the compounds was examined, and as a result it has been ascertained that there are no particularly noticeable practical problems in acute toxicity, skin-irritating property, skin-sensitizing property, mutagenic property, etc., and thus these compounds have high safety.

Ellagic acid series compounds in the invention as the essential component is used in an amount effective for giving a skin lightening and whitening effect and the amount depends on product form and frequency of use, but the compounds are made to be contained in various cosmetics usually in an amount of 0.001 to 20 weight % (hereinafter abbreviated as %), preferably in an amount of 0.005 to 5%.

The agents for external application of the invention can contain at least one additive conventionally used for external preparations.

For example, in order to further disperse ellagic acid series compounds, basic amino acids such as arginine or monosaccharides such as glucose can be added in an amount of 0.001 to 30%, preferably 0.005 to 20% in the invention. Further, besides the above components, there can be compounded in agents for external application of the invention raw materials ordinarily used in cosmetic, soaps or bath agents, for example, oils, water surfactants, humectants, lower alcohols, thickeners, antioxidants, chelating agents, pH-adjusting agents, antiseptics, perfume, coloring matters, ultraviolet absorbers, vitamins, amino acids, etc.

Specifically, examples of usable oils include fats and oils such as olive oil, Jojoba oil, castor oil, cacao butter, tsubaki oil, coconut oil, Japan wax, grapeseed oil, avocado oil, mink oil, egg yolk oil and hardened oils; waxes such as spermaceti, beeswax, lanolin, carnauba wax and candelilla wax; hydrocarbons such as liquid paraffin, ceresine, squalane, microcrystalline wax, paraffin wax and vaseline; fatty acids such as stearic acid, oleic acid, lauric acid, myristic acid, isostearic acid and behenic acid; alcohols such as cetanol, stearyl alcohol, lauryl alcohol, octyldodecanol and hexyldecanol; esters such as isopropyl myristate, butyl stearate, isopropyl palmitate, octyldodecyl myristate, octyldodecyl oleate and cholesterol oleate; and the like. Further, as usable surfactants, there can be mentioned amionic surfactants such as sodium stearate, sodium cetyl sulfate, polyoxyethylene lauryl ether phosphate, sodium lauryl phosphate, triethanol palmitate and sodium N-acylglutamate; cationic surfactants such as stearyldimethylbenzylammonium chloride and stearyltrimethylammonium chloride; ampholytic surfactants such as alkylaminoethylglycine hydrochloride solution and lecithin; nonionic surfactants such as glycerin monostearate, sorbitan monostearate, sucrose fatty acid esters, propylene glycol monostearate, polyoxyethylene oleyl ether, polyethylene glycol monostearate, polyoxyethylenesorbitan monopalmitate, polyoxyethylene coconut fatty acid monoethanolamide, polyoxyethylenepolyoxypropylene glycol, polyoxyethylene castor oil and polyoxyethylene lanolin; and the like. As humectants, there can be mentioned polyhydric alcohols such as glycerin, 1,3-butylene glycol, propylene glycol, sorbitol, polyethylene glycol and dipropylene glycol; NMF compounds such as amino acids, sodium lactate and sodium pyrrolidonecarboxylate; water soluble high molecular substances such as hyaluronic acid, collagen, mucosaccharides and chondroitin sulfate; and the like. As lower alcohols, there can be mentioned ethanol, isopropanol, etc. As thickeners, there can be mentioned natural high molecular substances such as sodium alginate, xanthane gum, aluminum silicate, quince seed extract, tragacanth gum and starch; semisynthetic high molecular substances such as methylcellulose, hydroxyethylcellulose, carboxymethylcellulose, soluble starch and cationized cellulose; synthetic high molecular substances such as carboxyvinyl polymers and polyvinyl alcohol; and the like. Usable antioxydants include dibutylhydroxytoluene, butylhydroxyanisole, propyl gallate and ascorbic acid; chelating agents include disodium edetate, ethane hydroxy diphosphate, pyrophosphates, hexametaphosphates, citric acid, tartaric acid and gluconic acid; pH-adjusting agents include sodium hydroxide, triethanolamine, citric acid, sodium citrate, boric acid, borax and disodium hydrogen phosphate; and antiseptics include methyl p-oxybenzoate, ethyl p-oxybenzoate, dehydroacetic acid, salicylic acid, benzoic acid, sorbic acid and benzalkonium chloride. Further, usable ultraviolet absorbers include 2-hydroxy-4-methoxybenzophenone, octyl p-dimethylaminobenzoate, ethylhexyl p-methoxycinnamate, titanium oxide, kaolin and talc; vitamins include vitamin A, vitamin B, vitamin C, vitamin D, vitamin E, vitamin F, vitamin K, vitamin P, vitamin U, carnitine, ferulic acid, γ-oryzanol, α-lipoic acid and orotic acid and their derivatives; and amino acids include glycine, alanine, valine, leucine, isoleucine, serine, threonine, phenylalanine, tyrosine, tryptophan, cystine, cysteine, methionine, proline, hydroxyproline, aspartic acid, glutamic acid, arginine, histidine and lysine and their derivatives. Optional components are not limited to those listed.

The agents for external application of the invention can be used in various product forms such as toilet water, cream, packing agent, lotion, skin milk and liquid cream, where the above essential component(s) and optional components are properly compounded.

There can specifically be mentioned as toilet waters compositions containing 0.01 to 2% essential component(s) of the invention 2 to 10% lower alcohol(s), 0.5 to 1% surfactant(s), 3 to 7% humectant(s), 0.05 to 0.2% pH-adjusting agent(s), 80 to 95% purified water, antiseptics (trace amount), coloring matter(s) (trace amount) and perfume(s) (trace amount); as skin creams compositions containing 0.01 to 2% essential component(s), 20 to 70% oil(s), 2 to 7% surfactant(s), 5 to 10% humectant(s), 11 to 73% purified water, antiseptic(s) (trace amount) and perfume(s) (trace amount); as lotions compositions containing 0.01 to 2% essential component(s), 5 to 10% lower alcohol(s), 0.5 to 2% surfactant(s), 2 to 8% humectant(s), 0.01 to 0.05% antioxidant(s), 0.02 to 0.1% chelating agent(s), 0.1 to 1% pH adjusting agent(s), 77 to 92% purified water, antiseptic(s) (trace amount) and perfume(s) (trace amount); as skin milks compositions containing 0.01 to 2% essential component(s), 20 to 40% oil(s), 2 to 5% surfactant(s), 53 to 78% purified water, antiseptic(s) (trace amount) and perfume(s) (trace amount); and as liquid creams compositions containing 0.01 to 2% essential component(s), 10 to 30% oil(s), 1 to 5% surfactant(s), 5 to 10% humectant(s), 53 to 84% purified water, antiseptics (trace amount) and perfume(s) (trace amount).

When the agents for external application of the invention are used as bath agents, there can further be added, besides the above components, at least one inorganic salt or inorganic acid such as sodium chloride, potassium iodide, ammonium chloride, sodium sulfate, sodium bicarbonate, sodium carbonate, sodium sesquicarbonate, aluminum sulfate, potassium sulfide, potassium sulfate, boric acid, borax, silicon dioxide, metasilicic acid, sodium sulfite, phosphoric acid, sodium hydrogenphosphate, potassium dihydrogenphosphate, sodium silicate, sodium polyphosphate, calcium hydrogenphosphate and sodium phosphate. Further, as necessary, there can be added, besides the above components, at least one of galenicals, binders, essential oils, protease and other components. These components are specifically exhibited below.

Galenicals

Atractylodes, *Atractylodis Rhizona*, Valerian, *Nepetae Herba*, Magnolia bark, Cnidium, Bitter orange pool, Japanese angelica root, Ginger, Scutellaria, Gardenia, *Artemisia vulgaris* var. vulgatissima (and var. indica), Aloe, Ginseng, Cinnamon bark, Peony root, Japanese peppermint leaf, Scutellaria, Hoelen, Japanese iris, *Schizandra nigra* Maxim, *Angelicae Dahuricae* Radix (Paichi), Saffon, Cork tree bark, Fennel, *Aurantii Nobilis Pericarpium*, *Lychnis coronata* Thumb, *Matricaria chamomilla* L., Chinese radish, willow, camphor tree, elderberry, *Sambucus zavanica* Reinw, *Fatsia japonica, Acorus gramineus* Soland, mugwort, *Hypericum erectum* Thunb, citron, bitter orange, peach, honey locust, loquat, Lonicera japonica Thunb, *Angelica dahurica*, bo tree, horse chestnut, milfoil, hop, rosemary, *Gracilaria textorii* suringar, pine, *Lantana camara* L., Licorice, *Valerianae japonicae* Radix, horse chestnut, etc. These may be in the form of either powder or extract.

Binders

Casein, carboxymethylcellulose sodium, water soluble gelatin, pectin, starch, methylcellulose, ethylcellulose, sodium alginate, polyvinyl alcohol, polyvinylpyrrolidone, polyvinylmethyl ether, polyethylene glycol, Karaya gum, Locust bean gum, tragacanth gum, carrageenan, Carbopol ®, acacia gum, agar.

Essential Oils

Japanese peppermint oil, jasmine oil, camphor oil, hinoki oil, tohi oil, turpentine oil, cinnamon oil, bergamot oil, mandarin oil, iris oil, pinneapple oil, lavender oil, bay oil, clove oil, hiba oil, rose oil, eucalyptus oil, lemon oil, thyme oil, peppermint oil, rosemary oil, sage oil, menthol, cineole, eugenol, citral, citronellal, borneol, linaloe oil, geraniol, camphor, thymol, spilanthole, pinene, limonene, terpane series compounds, etc.

Protease

Pepsin, trypsin, chymotrypsin, cathepsin, papain, protaminase, ficin and proteases derived from bacteria, yeasts and molds, etc.

Agents for external application containing the above components include as bath agents compositions containing 0.02 to 10% to essential component(s), inorganic salt(s), inorganic acid(s) (balance), perfume(s) and coloring matter(s) (trace); as body shampoos compositions containing 0.02 to 10% essential component(s), 5 to 40% surfactant(s), 1 to 20% humectant(s), 0.5 to 5% thickener(s), 0.05 to 0.5% chelating agent(s), purified water (balance), perfume(s) and coloring matter(s) (trace; and as body rinses compositions 0.02 to 10% essential compoent(s), 5 to 30% oil(s), 0.5 to 5% surfactant(s), 0.1 to 10% humectant(s), purified water (balance), antiseptic(s) (trace) and perfume(s) (trace).

The agents for external application having much better skin lightening and whitening effect than ordinary products and also having extremely high safety are provided according to the present invention.

The agents for external application free from bad dispersion and having an excellent product appearance and stability in preservation are provided according to the invention directed to use of alkali metal salt of the ellagic acid series compound.

Thus, the agents for external application of the invention can suitably be used, especially as agent to be applied to in various product forms such as various cosmetics creams, liquid creams, toilet waters, beauty essences, packs, powders, lip creams, lipsticks, under makeups, foundations, suncares, bath agents, body shampoos, body rinses, soaps, cleansing foams, ointments, jelly agents and aerosols.

The present invention is explained below by nonlimitative examples.

EXAMPLE 1

Toilet waters containing 1% of the respective components in Table 1, 50% of ethanol and the balance of pure water were prepared, and decoloring effect was tested according to the following method. The results are shown in Table 1.

Decoloring Effect Test

The hair was removed from the back of colored guinea pigs (each group consisting of 3 animals), and 50μl of the toilet waters were respectively applied once a day, 5 times a week, to the area of about 4 cm² for 3 weeks. Four days after the end of the treatment, skin color was measured by a color-difference meter.

TABLE 1

|  | Component | Before the test | After the test |
|---|---|---|---|
| Product of the invention | Ellagic acid | 36.1 | 45.4 |
|  | 3,4-Di-O-methylellagic acid | 36.1 | 44.0 |
| Comparative example | Quercetin | 36.1 | 41.0 |
|  | Catechin | 36.1 | 40.0 |
|  | Kojic Acid | 36.1 | 42.5 |
|  | — | 36.1 | 36.1 |

Values in the table mean L values (brightness), and it is meant that the greater the value, the whiter the skin.

It is seen from the result shown in Table 1 that the toilet waters of the invention containing the ellagic acid series compounds have a better decoloring effect than the toilet waters respectively containing quercetin, catechin and kojic acid.

EXAMPLE 2

Creams respectively having the compositions shown in Table 2 were prepared and applied respectively onto pigment macula parts of 5 human beings having pigment maculas (blotch) 2 to 3 times a day for one month, and then the brightness of the pigment macula parts was measured by a color-difference meter. The results are shown in Table 2.

EXAMPLE 3

Preparation of an Alkali Metal Salt of Ellagic Acid

Commercially available ellagic acid (manufactured by Tokyo Kasei Kogyo Co., Ltd.) (25.6 g) was stirred and dispersed in 500 g of purified water, 500 g of 1N-sodium hydroxide was added to make a solution, 5 g of active carbon was added thereto, and the mixture was stirred at room temperature for 30 minutes. The resulting suspension was filtered under reduced pressure to obtain a reddish brown supernatant, to which was dropwise added concentrated sulfuric acid to adjust the pH to 7.0, whereby a precipitate was deposited. The precipitate was collected using a high speed centrifugal separator (8000 rpm, 5 minutes), washed successively with water and ethanol, and dried to obtain 24.8 g of sodium ellagate.

Cosmetic Cream

Alkali metal salts of ellagic acid having different pH values were prepared respectively in a similar manner to that described above, and their water dispersibility, and appearance and stability over a day's lapse were evaluated in creams into which these compounds had been compounded. Water dispersibility was evaluated using the 1% aqueous solutions, and evaluation of the creams was carried out with adjustment of pH to 5.5 to 6 with citric acid and sodium citrate. The composition of the cosmetic creams was as follows:

Cream Composition 5.0 weight % liquid paraffin (#70), 15.0% squalane, 5.0% cetostearyl alcohol, 2.0% beeswax, 2.0% glycerin monostearate, 2.0% POE (20) sorbitan monolaurate, 0.1% propylparaben, 0.2% methylparaben, 0.5% ellagate, purified water (balance), perfume (appropriate amount).

TABLE 2

|  | Component | Product I of the invention | Product II of the invention | Comparative example |
|---|---|---|---|---|
| Composition | Ellagic acid | 0.25% | — | — |
|  | 3,4-Di-O-methylellagic acid | — | 0.25% | — |
|  | Stearic acid | 2.5 | 2.5 | 2.5% |
|  | Cetanol | 1.5 | 1.5 | 1.5 |
|  | Vaseline | 5.0 | 5.0 | 5.0 |
|  | Liquid paraffin | 10.0 | 10.0 | 10.0 |
|  | Polyethylene glycol 1500 | 3.0 | 3.0 | 3.0 |
|  | Glycerin | 1.0 | 1.0 | 1.0 |
|  | Antiseptic | Trace | Trace | Trace |
|  | Perfume | Trace | Trace | Trace |
|  | Purified water | Balance | Balance | Balance |
| Performance | Before the test | 44.5 | 44.4 | 44.5 |
|  | After the test | 50.0 | 48.0 | 44.1 |

Values in the table near brightness.

It is seen from the results of Table 2 that the ellagic acid and 3,4-Di-0-methylellagic acid-compounded creams clearly reduced the pigment maculas as compared with the cream not containing these compounds (comparative example). No irritating property or allergic reaction was observed for the products of the invention.

TABLE 3

|  | Treatment pH | dispersibility | appearance |
|---|---|---|---|
| Sodium ellagate | 6 | Uniformly dispersed | No change |
|  | 7 | Uniformly dispersed | No change |
|  | 9 | Uniformly dispersed | The upper layer of the cream got discolored to brown with day lapse |
| Potassium ellagate | 5 | Uniformly dispersed | No change |

| Ellagate Treatment pH | Water dispersibility | Change in appearance |
|---|---|---|
| 8 | Uniformly dispersed | No change |

As is seen from Table 3, the alkali metal salts of ellagic acid as obtained by collecting the precipitates with adjustment of pH to 5 to 8 have a good water dispersibility, and are excellent in stability with day's lapse after compounding into the products.

EXAMPLE 4

In order to demonstrate improvement in fresh effect, pigment deposits were made on the backs of Fl guinea pigs by UVB irradiation, and cosmetic creams were applied onto these parts to investigate the reducing effect on the pigment deposit.

The test method was as follows:

(1) The same creams as prepared in Example 3 were used except that ellagates were compounded in an amount of 1% respectively. The pH of the creams was adjusted to 5.0 to 5.5.

(2) Test of reducing effect on the pigment deposit

The hair on the backs of Fl guinea pigs (each group consisting of 5 animals) was cut. The resulting backs were irradiated with UVB (ultraviolet ray) of ½ MED amount once a day for one week. After deposit of pigment, the backs were daily coated respectively with 0.1 g of the creams in the area of about 4 cm² once a day for 5 weeks, and changes in the skin color were measured by a color-difference meter (L value). The results are shown in Table 4.

TABLE 4

| | Sample | | | L value before the test | L value 5 weeks thereafter | (Improvement degree) |
|---|---|---|---|---|---|---|
| Comparative Example | No UVB irradiation, cream type coating (Control) | | | 33.2 | 33.6 | |
| | UVB irradiation | Non Coating with cream | | 25.3 | 28.0 | Δ2.7 |
| | | Coating with cream (no compounding of ellagic acid) | | 25.9 | 30.6 | Δ4.7 |
| Product of the invention | | Ellagic acid | | 25.8 | 31.9 | Δ6.1 |
| | | Sodium ellagate | pH 5 treated product | 25.5 | 32.6 | Δ7.1 |
| | | | pH 7 treated product | 25.5 | 33.7 | Δ8.2 |
| | | | pH 8 treated product | 25.3 | 33.1 | Δ7.8 |
| | | Potassium ellagate | pH 6 treated product | 25.7 | 33.2 | Δ7.5 |

Note) Values in the table mean L values (brightness), and it is meant that the larger the value, the whiter the skin.

It is seen from the results in Table 4 that the creams of the invention where the alkali metal salts of ellagic acid were compounded clearly have an embraced L value as compared with the creams where no such salt was compounded or ellagic acid itself was compounded, and are superior to the latter creams in reducing effect on pigment deposit.

EXAMPLE 5

Various external preparations of the invention are illustrated below.

| Toilet water 1 | |
|---|---|
| 3,3',4-tri-O-methylellagic acid | 0.1% |
| Glycerin | 4.0 |
| Ethanol | 10.0 |
| Carboxyvinyl polymer | 0.5 |
| Perfume | trace |
| Purified water | balance |
| Toilet water 2 | |
| 3-Ethyl-4-methyl-5-hydroxyellagic acid | 0.1% |
| Glycerin | 4.0 |
| Ethanol | 10.0 |
| Carboxyvinyl polymer | 0.5 |
| Perfume | trace |
| Purified water | balance |
| Toilet water 3 | |
| Sodium ellagate | 0.05% |
| Glycerin | 3.0 |
| Ethanol | 6.0 |
| Perfume | trace |
| Purified water | balance |
| Toilet water 4 | |
| A. Ethyl alcohol phase part | |
| Ethyl alcohol | 10.0% |
| POE(80) hardened castor oil | 0.3 |
| Tocopherol | 0.1 |
| Methylparaben | 0.1 |
| Perfume | appropriate amount |
| B. Water phase part | |
| Potassium ellagate (treated pH 5) | 0.05% |
| Glycerin | 3.0 |
| Purified water | balance |

Toilet water was prepared by making a uniform solution consisting of the above prescription A, and adding the solution by portions to the water phase B with stirring.

| Emulsion 1 | |
|---|---|
| A. Oil phase part | |
| Liquid paraffin (#70) | 10.0% |
| Isopropyl myristate | 2.0 |
| Glycerin monostearate | 0.5 |
| Stearic acid | 2.0 |
| POE(20) stearyl alcohol | 0.7 |
| Glycyrrhetinic acid | 0.1 |
| Butylparaben | 0.1 |
| B. Water phase part | |
| Sodium ellagate (treated pH 6) | 0.5% |
| Glycerin | 2.0 |
| Carbopol ® 941 | 0.1 |
| Ethanol | 10.0 |
| Methylparaben | 0.1 |
| Purified water | balance |
| C. Perfume | appropriate amount |

The above compositions A and B were respectively mixed at 70° C. to make solutions, and then A was added to B and the mixture was uniformly emulsified.

Further, C was added thereto, followed by cooling to prepare an emulsion.

| Emulsion 2 | |
|---|---|
| Ellagic acid | 0.5% |
| Stearic acid | 1.0 |
| Cetanol | 2.0 |
| Vaseline | 2.5 |
| Squalane | 4.0 |
| L-arginine | 1.0 |
| Lipophilic type glycerin monostearate | 1.0 |
| Glycerin | 2.0 |
| Potassium hydroxide | 0.1 |
| Perfume | trace |
| Purified water | balance |

| Pack | |
|---|---|
| A. Ethyl alcohol phase part | |
| Ethyl alcohol | 10.0% |
| Polyvinyl alcohol | 15.0 |
| Propylene glycol | 3.0 |
| Methylparaben | 0.1 |
| Butylparaben | 0.05 |
| Glycyrrhetinic acid | 0.1 |
| B. Water phase part | |
| Sodium ellagate (treated pH 8) | 1.0% |
| Carboxymethylcellulose sodium | 5.0 |
| POE(15) oleyl ether | 1.0 |
| Purified water | balance |
| C. Perfume | appropriate amount |

The above prescriptions A and B were mixed and uniformly mixed with heating to 70° C. The prescription C was added while cooling the mixture to prepare a pack.

| Cosmetic cream | |
|---|---|
| A. Oil phase part | |
| Liquid paraffin (#70) | 5.0% |
| Squalane | 15.0 |
| Cetostearyl alcohol | 5.0 |
| Beeswax | 2.0 |
| Glycerin monostearate | 2.0 |
| POE(20) sorbitan monolaurate | 2.0 |
| Propylparaben | 0.1 |
| B. Water phase part | |
| Sodium ellagate (treated pH 7) | 0.5% |
| Hyaluronic acid | 0.2 |
| Methylparaben | 0.2 |
| Purified water | balance |
| C. Perfume | Appropriate amount |

The above prescriptions A and B were respectively mixed at 70° C. to make solutions, A was added to B and the mixture was uniformly emulsified. Further C was added thereto, followed by cooling to prepare a cream.

| Bath agent 1 (granular state) | |
|---|---|
| Sodium bicarbonate | 49% |
| Sodium sulfate | 46.5 |
| Sodium ellagate (treated pH 8) | 1 |
| Carboxymethylcellulose sodium | 1 |
| Lanolin | 0.5 |
| Coloring matter | 0.5 |
| Perfume | 1.5 |
| Total | 100% |

| Bath agent 2 (granular state) | |
|---|---|
| Potassium bicarbonate | 63.9% |
| Sodium sulfate | 30.0% |
| Sodium ellagate (treated pH 8) | 1.0 |
| Magnesium oxide | 2.0 |
| Carboxymethylcellulose sodium | 1.0 |
| *Matricaria chamomilla* L. | 0.5 |
| Vitamin E | 0.5 |
| Perfume | 1.0 |
| Coloring matter | 0.1 |
| Total | 100.0% |

| Bath agent 3 (powdery state) | |
|---|---|
| Sodium bicarbonate | 50% |
| Sodium carbonate | 3 |
| Sodium sulfate | 43.5 |
| Sodium ellagate (treated pH 8) | 1 |
| Liquid paraffin | 0.5 |
| Coloring matter | 0.5 |
| Perfume | 1.5 |
| Total | 100% |

| Bath agent 4 (powdery state) | |
|---|---|
| Sodium bicarbonate | 32.1% |
| Sodium carbonate | 60.0 |
| Potassium ellagate (treated pH 7) | 2.0 |
| Pepsin yeast (200U) | 1.0 |
| Sodium citrate | 3.0 |
| Limonene | 0.5 |
| Lavender oil | 0.3 |
| Perfume | 1.0 |
| Coloring matter | 0.1 |
| Total | 100.0% |

| Bath agent 5 (tablet) | |
|---|---|
| Sodium bicarbonate | 25.4% |
| Sodium carbonate | 30.0 |
| Succinic acid | 40.0 |
| Sodium ellagate (treated pH 7) | 2.0 |
| Edible seaweed | 0.5 |
| *Ecklonia cava* kjellman | 0.5 |
| Aloe powder | 0.5 |
| Perfume | 1.0 |
| Coloring matter | 0.1 |
| Total | 100.0% |

| Bath agent 6 (Effervescent tablet) | |
|---|---|
| Sodium sulfate | 8% |
| Sodium bicarbonate | 30 |
| Sodium carbonate | 19 |
| Sodium ellagate (treated pH 5) | 1 |
| Citric acid | 20 |
| Tartaric acid | 10 |
| Succinic acid | 10 |
| Coloring matter | 0.5 |
| Perfume | 1.5 |
| Total | 100% |

| Bath agent 7 (Liquid state) | |
|---|---|
| Propylene glycol | 50 |
| Ethanol | 20 |
| Sodium sulfate | 5 |
| Sodium ellagate (treated pH 6) | 1 |
| Lanolin | 0.5 |
| Avocado oil | 0.5 |
| Coloring matter | 0.5 |
| Perfume | 1.5 |
| Pure water | 21 |
| Total | 100% |

| Body shampoo | |
|---|---|
| Potassium salt of coconut fatty acid | 5.0% |
| Potassium oleate | 20.0 |
| Diethanolamide of coconut fatty acid | 3.0 |
| Glycerin | 10.0 |
| Sodium sulfate | 2.0 |
| EDTA | 0.1 |
| Sodium ellagate (treated pH 7) | 2.0 |
| Perfume | appropriate amount |
| Coloring matter | appropriate amount |
| Antiseptic | appropriate amount |
| Purified water | balance |

| Body rinse | |
|---|---|
| Liquid paraffin | 10.0% |
| Isopropyl palmitate | 3.0 |
| Methylpolysiloxane | 3.0 |
| Glycerin monostearate | 1.5 |

| -continued | |
|---|---|
| POE glycerin stearate | 1.5 |
| Glycerin | 5.0 |
| Potassium ellagate (treated pH 7) | 1.0 |
| Perfume | appropriate amount |
| Coloring matter | appropriate amount |
| Antiseptic | appropriate amount |
| Purified water | balance |

What is claimed is:

1. A method of lightening and whitening human skin, comprising applying to the human skin a composition comprising an effective amount of at least one ellagic acid series compound represented by formula I:

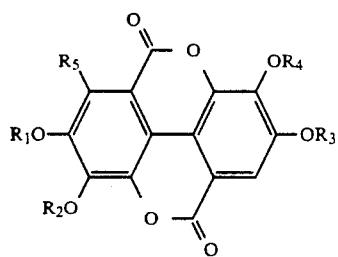

wherein $R_1$ to $R_4$ are the same or different and represent a hydrogen atom, an alkyl group having 1 to 20 carbon atoms, an alkoxy group having 1 to 20 carbon atoms, a polyalkylene oxide residue where the alkylene oxide unit has 2 to 3 carbon atoms, or a sugar residue represented by the formula II:

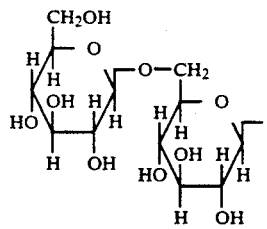

and wherein $R_5$ is a hydrogen atom, a hydroxyl group or an alkoxy group having 1 to 8 carbon atoms, or a salt thereof.

2. The method of claim 1 wherein the ellagic acid series compound is in the form of a salt.

3. The method of claim 1, wherein $R_1$ to $R_5$ in the formula I are hydrogen atoms.

4. The method of claim 1, wherein $R_1$ to $R_4$ are hydrogen atom, methyl group or ethyl group and $R_5$ is hydrogen atom, hydroxyl group or methoxy group.

5. The method of claim 1, wherein the ellagic acid series compound is applied to the human skin in an amount of 0.001 to 20% by weight.

6. The method of claim 5, wherein the composition further contains a basic amino acid or monosaccharide in an amount of 0.001 to 30% by weight.

7. The method of claim 5, wherein the composition further contains 20 to 40 weight % of oil and 2 to 5 weight % of surfactant.

8. The method of claim 5, wherein the composition further contains 20 to 70 weight % of oil, 2 to 7 weight % of surfactant and 5 to 10 weight % of humectant.

9. The method of claim 2, wherein the salt is a partially neutralized salt.

10. The method of claim 2, wherein the salt is an alkali metal salt.

* * * * *